United States Patent [19]

Simmons

[11] Patent Number: 5,587,537

[45] Date of Patent: Dec. 24, 1996

[54] METHOD AND APPARATUS FOR WELD TESTING

[75] Inventor: Frederick H. G. Simmons, Fergus, Canada

[73] Assignee: Alcatel Canada Wire Inc., North York, Canada

[21] Appl. No.: 393,694

[22] Filed: Feb. 24, 1995

[30] Foreign Application Priority Data

Mar. 15, 1994 [CA] Canada ................................. 2119061

[51] Int. Cl.⁶ ........................................................ G01L 5/04
[52] U.S. Cl. ............................ 73/862.392; 73/862.474
[58] Field of Search .............................. 73/827, 831, 850, 73/862.391, 862.392, 862.42, 862.451, 862.474; 228/103, 104; 29/868, 869

[56] References Cited

U.S. PATENT DOCUMENTS

| | | | |
|---|---|---|---|
| 2,362,626 | 11/1944 | Giffen | 73/862.392 |
| 4,027,529 | 6/1977 | Olsen | 73/827 |
| 4,402,229 | 9/1983 | Byrne | 73/862.392 |
| 4,677,856 | 7/1987 | Fischer | 73/850 |
| 4,803,888 | 2/1989 | Choquet | 73/862.392 |
| 4,893,944 | 1/1990 | Leroux | 73/827 X |
| 4,960,001 | 10/1990 | Vemmer | 73/862.392 |
| 5,038,622 | 8/1991 | Tijmann | 73/862.392 X |
| 5,291,423 | 3/1994 | Roosli | 73/850 X |
| 5,415,047 | 5/1995 | Maciejewski et al. | 73/850 |

FOREIGN PATENT DOCUMENTS

| | | | |
|---|---|---|---|
| 4250334 | 9/1992 | Japan | 73/850 |
| 1093942 | 5/1984 | U.S.S.R. | 73/850 |
| 1481629 | 5/1989 | U.S.S.R. | 73/850 |

*Primary Examiner*—Richard Chilcot
*Assistant Examiner*—Elizabeth L. Dougherty
*Attorney, Agent, or Firm*—Ware, Fressola, Van Der Sluys & Adolphson

[57] ABSTRACT

The quality of a weld is tested in an elongated object, such as a strand or cable, by pressing the ends to be welded against one another and maintaining them in such pressed condition while welding the same. Thereafter, a predetermined tension is applied to the weld and the elongation produced thereby is measured and compared to a preset value. If the elongation exceeds the preset value, the weld is considered unsatisfactory.

20 Claims, 7 Drawing Sheets

METHOD AND APPARATUS FOR WELD TESTING

BACKGROUND OF THE INVENTION

1. Field of the Invention

This invention relates to a method and an apparatus for measuring the quality or strength of an end-to-end weld in an elongated object such as a strand or cable, particularly the conductor in an electrical cable.

2. Description of the Prior Art

It is often necessary to weld elongated objects end-to-end to provide continuity in such objects. This is normally done as part of a continuous operation. In the manufacture of electrical cables, such operations include Catenary Continuous Vulcanization (CCV) or Vertical Continuous Vulcanization (VCV) and normally use a welding technique known as upset welding or "butt welding". This is done by placing the two ends of the conductor within a ceramic bushing so that they would contact each other, clamp these ends in such position and weld them within the bushing by upset welding in a known manner. When the welding is complete, the operator would release the clamps, break the ceramic bushing, and allow the conductor to proceed to further operations, such as jacketing or the like.

The problem in the above system is that the quality or strength of the weld is not known and consequently breaks of the weld can occur during subsequent operations or during installation of the cable.

An object of the present invention is to obviate the above problem and to provide a method and an apparatus for testing the quality or strength of the weld immediately after such weld has been made.

Other objects and advantages of the invention will be apparent from the further description thereof.

SUMMARY OF THE INVENTION

Basically the method for measuring the quality of an end-to-end weld in accordance with the present invention comprises pressing the ends to be welded against one another and maintaining them in such pressed condition to ensure that no space is created between said ends as metal is displaced during welding and then welding said ends in a known manner. The weld could be made, for example, by electric upset welding which is performed within a ceramic bushing with the time and voltage being controlled automatically as a result of settings made by the operator. The weld is then normally cooled. After the weld has been cooled, a predetermined tension is applied to the weld and the elongation produced thereby is measured, for instance with strain gauges. The tension can be applied by the same means which are used to maintain the ends pressed against each other during the welding operation, such as, for example hydraulic or pneumatic cylinders. The elongation thus measured is compared with a preset value, namely to the elongation that would be produced under the same conditions in a normal elongated object of the same cross section, i.e. an object without a weld therein. The comparison is normally done by a computer and would indicate to the operator whether the weld is satisfactory or not.

Such a method is particularly applicable to elongated objects such as strands or cable, especially the conductor in an electrical cable, where it is important to have a good quality weld, and obviously the tension applied to each such strand or conductor will depend to a large extent on the size or diameter thereof.

The apparatus of the present invention, for measuring the quality of an end-to-end weld in an elongated object, such as a strand or a cable, comprises: means for pressing the ends to be welded against one another; means for maintaining said ends in such pressed condition during welding; means for welding such ends; means for applying a predetermined tension to the resulting weld; means for measuring the elongation obtained as a result of said tension; and means for comparing said elongation to a preset value which is an elongation expected under the same conditions of the same size object that has not been welded.

The means for pressing the ends against one another are preferably hydraulic or pneumatic cylinders, although other suitable means can also be used. The same means can also be employed to exert a predetermined tension on the weld once the weld has been made. Furthermore, the means for maintaining the ends in the pressed condition during welding can also be hydraulic or pneumatic cylinders provided with suitable clamps to securely clamp the object on each side of the weld when required.

The means for welding the ends will normally include a ceramic bushing around said ends where the weld is created. This is usually controlled automatically as a result of time and voltage settings made by the operator on a computer. The ceramic bushing is normally held in place by a pair of clamps. Once the welding is done, the weld is normally cooled off.

The means for measuring the elongation obtained as a result of the tension applied to the weld could comprise an encoder which would readily measure the elongation, for example, between the two clamps holding the object at each side of the weld. The obtained measurement data would then normally be transmitted to a computer which would compare it with a preset value for the given size of the object and determine whether the weld is satisfactory or not. If potential weld failure is indicated, the welding procedure could be repeated until a satisfactory weld is achieved.

BRIEF DESCRIPTION OF THE DRAWINGS

The invention will now be described with reference to the appended drawings in which.

DETAILED DESCRIPTION OF THE INVENTION

Figure 1:
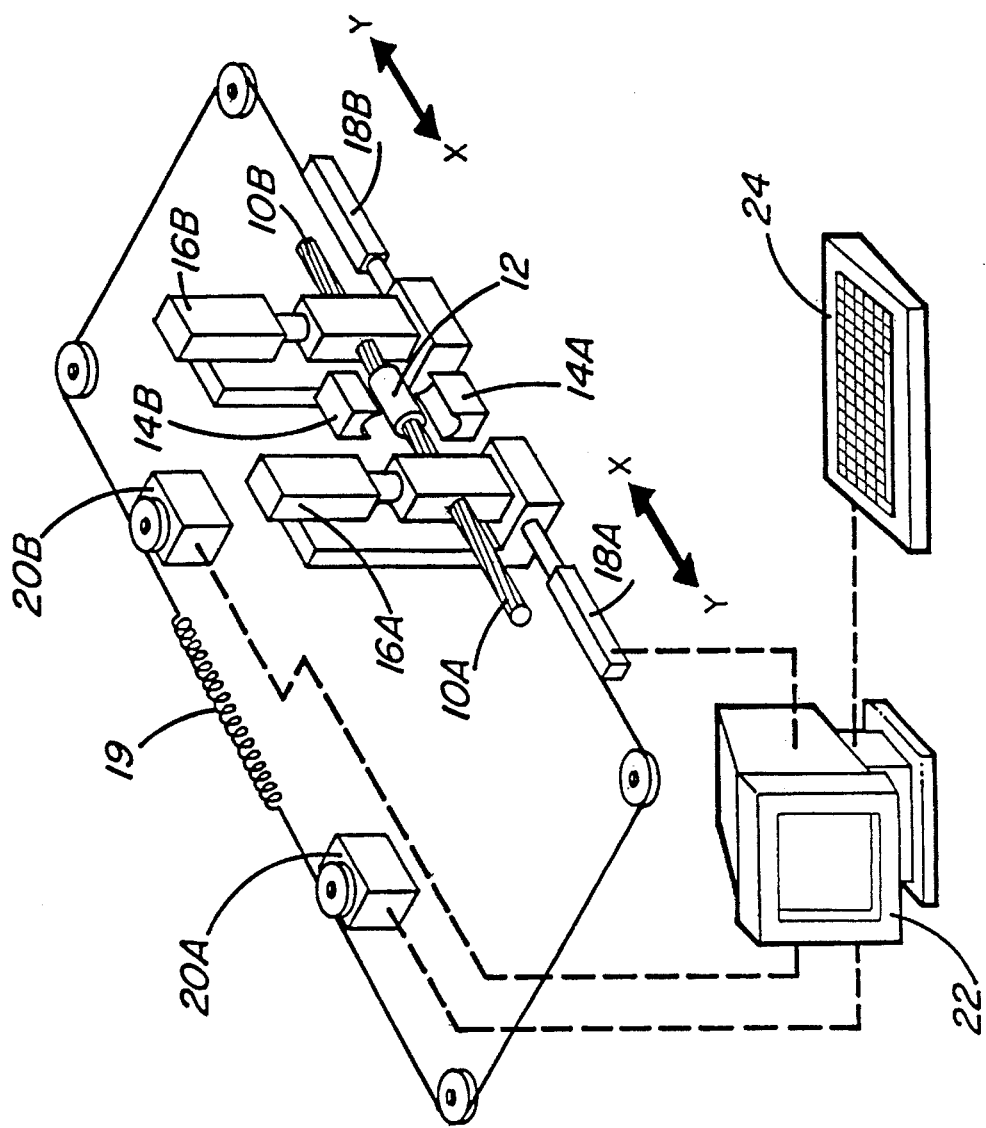
FIG. 1 is a diagrammatic representation, in perspective, of an embodiment of the present invention illustrating the apparatus and the steps of the method.

As shown in FIG. 1, strand 10A is welded to strand 10B within a ceramic bushing 12 which, during welding, is held in place by clamps 14A and 14B. Cylinders 16A and 16B clamp strands 10A and 10B respectively to maintain them pressed against one another within the bushing 12. Cylinders 18A and 18B are used to provide the upset pressure, in direction "X", to press the two ends to be welded against one another and this pressure is maintained during welding to ensure that no space is created between the welds as metal is displaced. The time and voltage for the weld is controlled automatically as a result of settings made by the operator.

Figure 2:
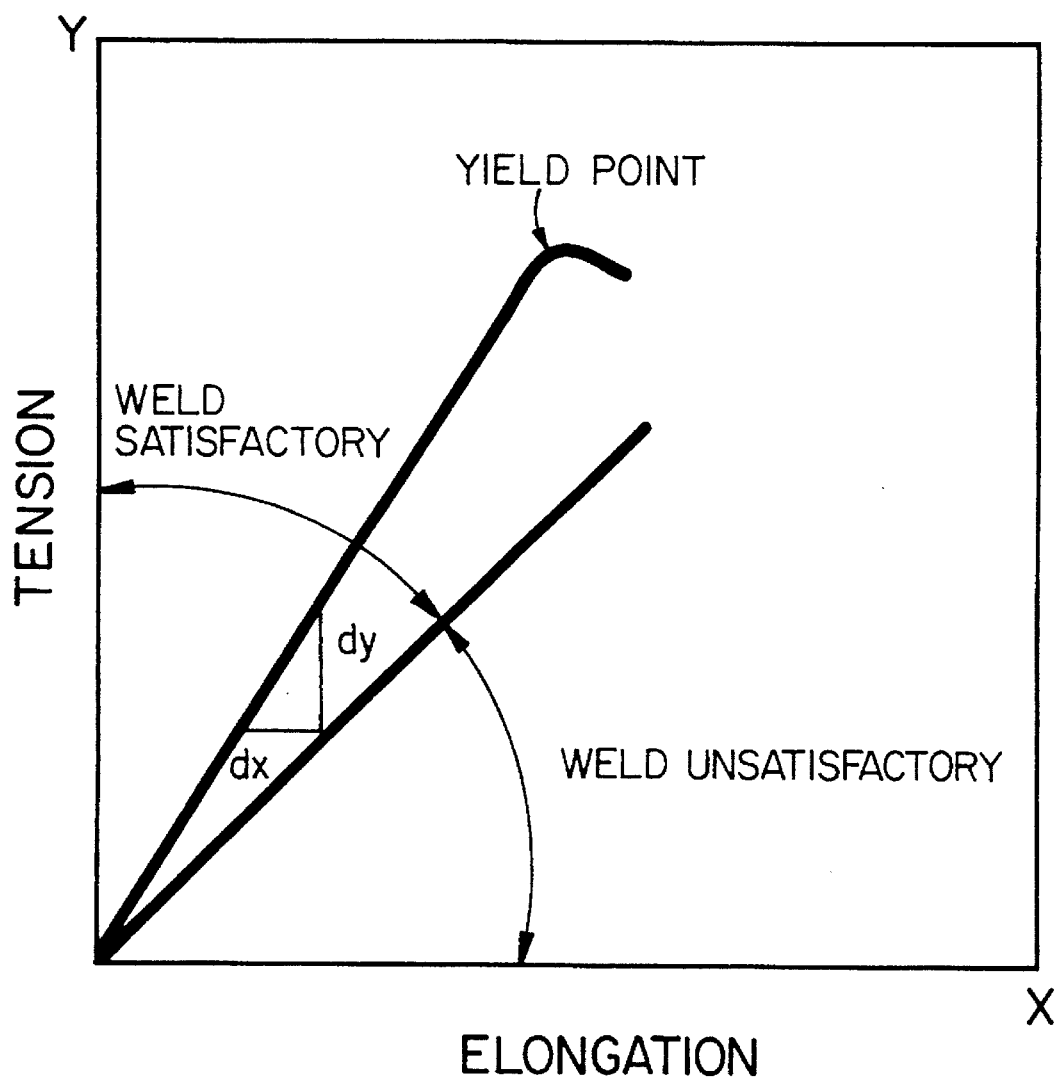
FIG. 2 is a graph of a stress to elongation curve that can be used to determine whether the weld is satisfactory or not.

Once the weld has been made, it is then normally cooled off. Usually, at this stage, clamps 14A and 14B as well as 16A and 16B would be released and the operator would break the ceramic bushing and the welded strand 10 (which is a combination of 10A and 10B) would proceed to further operations such as jacketing or winding or the like. However, according to the present invention, at this stage, the clamp pressure of clamps 16A and 16B would be maintained and a predetermined tension would be applied to the weld in direction "Y" with cylinders 18A and 18B. The elongation or displacement of these clamps, produced by this tension, can be measured by spring 19 (or other types of strain gauges) and encoders 20A and 20B and the results of the measurements are communicated to the computer 22 which compares them with preset values that were entered into the computer through keyboard 24 for various sizes of the strand 10. This comparison is normally done by means of load vs elongation curves. Essentially, the strand is not tested to destruction, but the elongation and tension enable the construction of a curve or rate of elongation dx/dy which is compared to the proportional part of the graph as shown in FIG. 2. When the results developed by the computer 22 would indicate a curve in the failure zone, the operator would be advised of a potential weld failure. Some specific examples of this will now be provided.

EXAMPLES

Five welds were made using the same copper strand, but the settings were adjusted by the operator to produce progressively better welds. The quality of the welds in the five specimens was then measured in accordance to the present invention. The results are shown in FIGS. 3 to 7 respectively produced by the computer, where FIG. 3 relates to specimen 1, FIG. 4 to specimen 2, FIG. 5 to specimen 3, FIG. 6 to specimen 4 and FIG. 7 to specimen 5.

Figure 3:
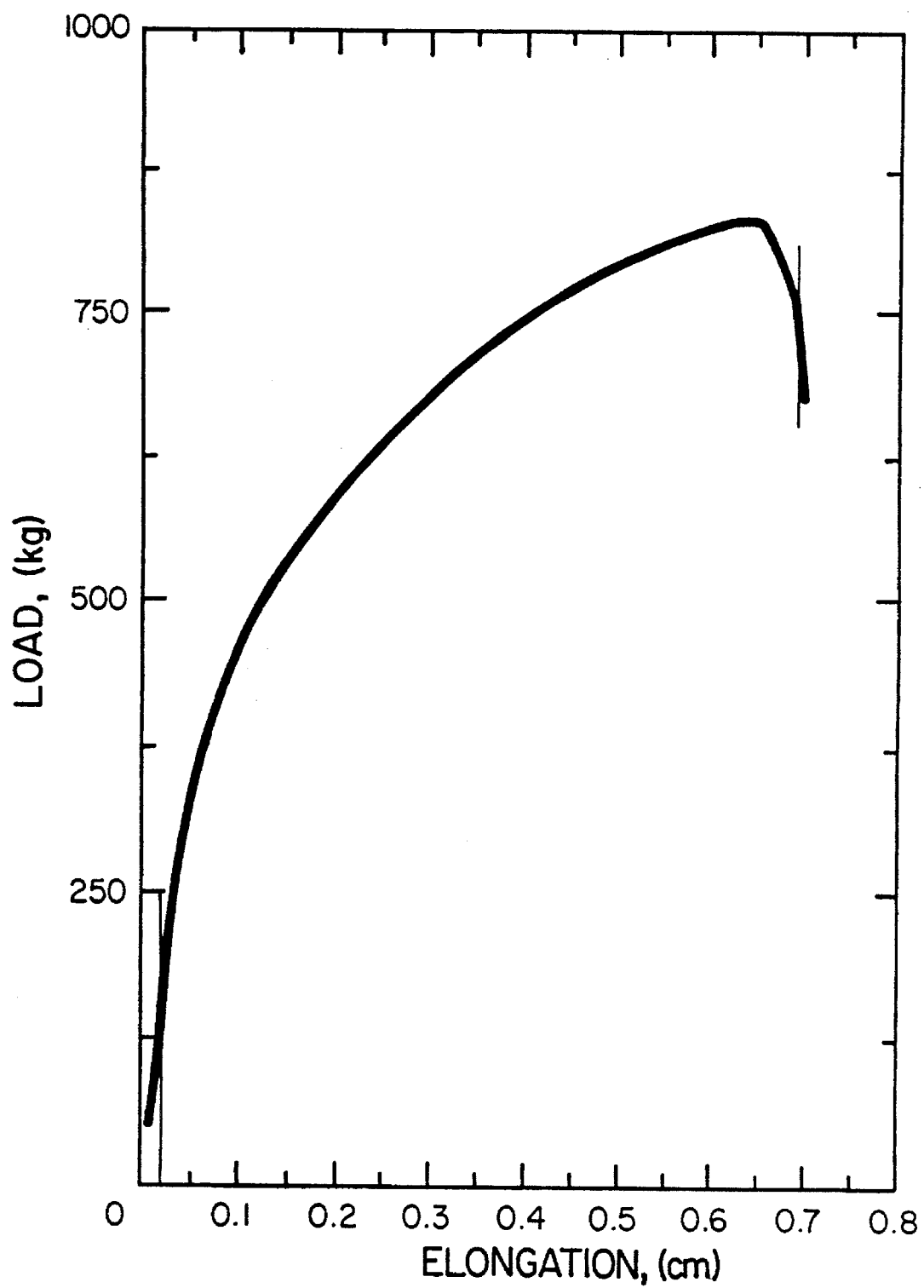
FIGS. 3 to 7 are graphs showing specific representations of the behavior of welds as set out in the examples provided further in this specification.
Figure 4:
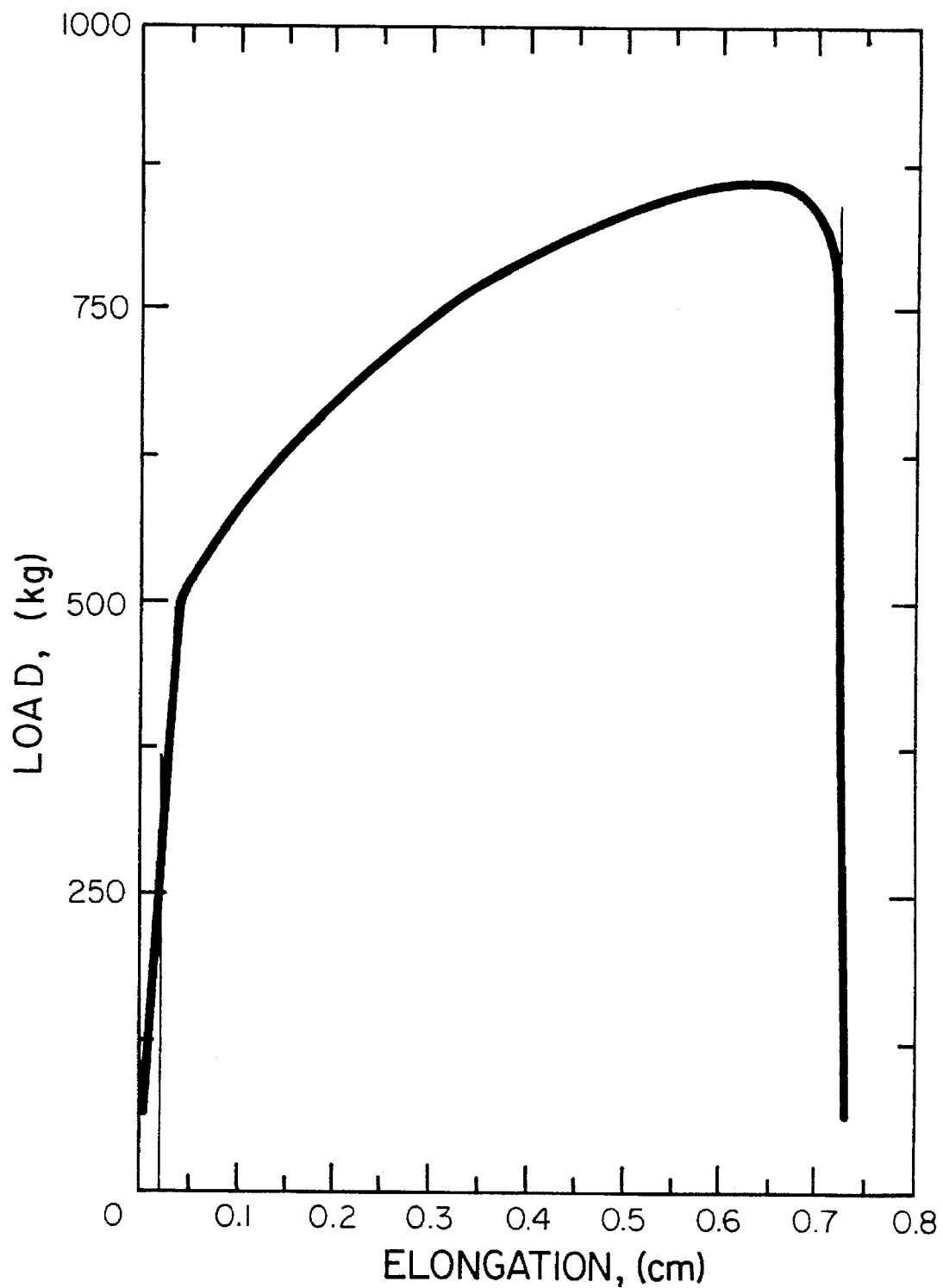
Figure 5:
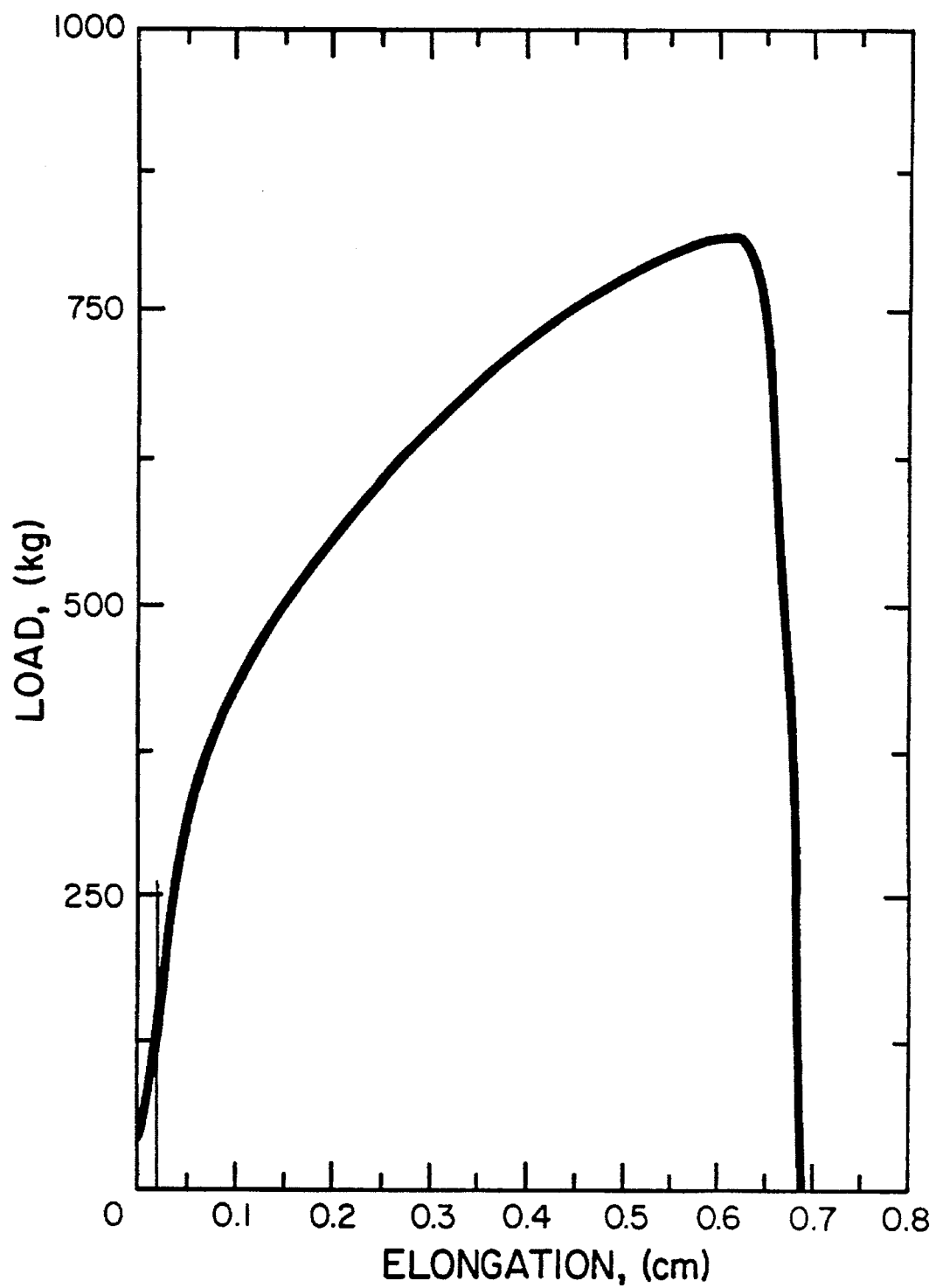
Figure 6:
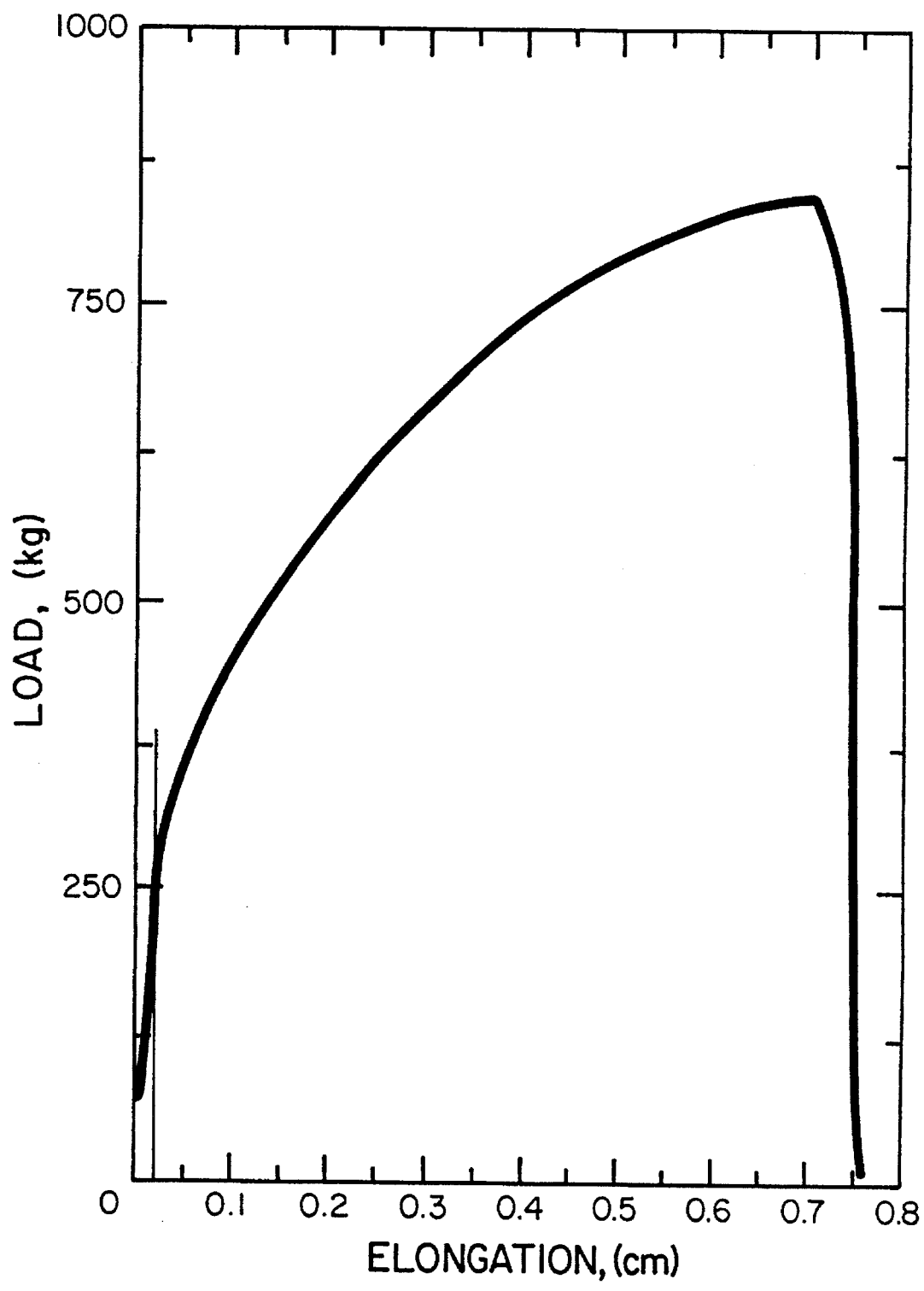
Figure 7:
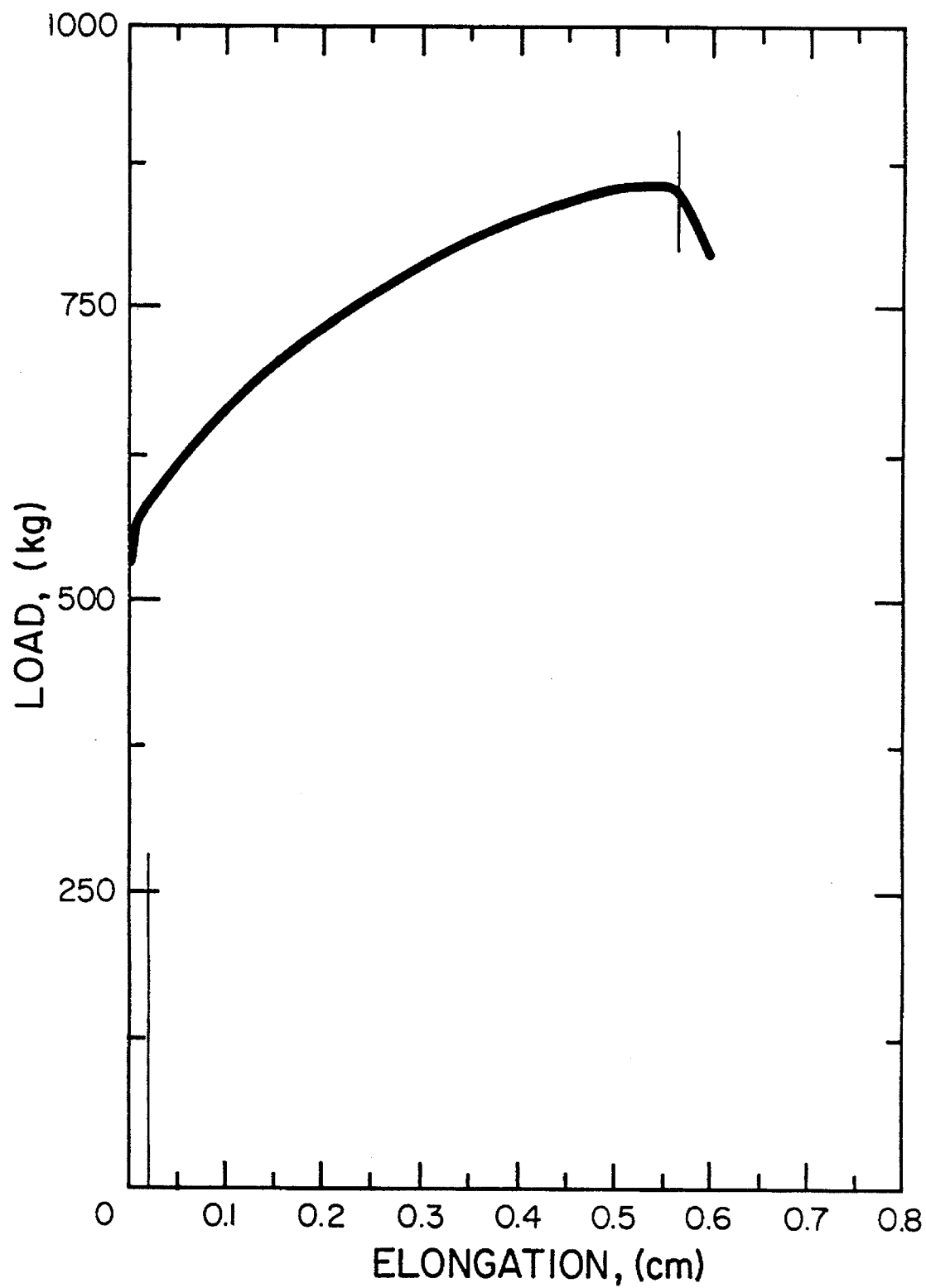

These results confirm and demonstrate that a good weld, such as that of specimen 5 shown in FIG. 7, has zero elongation even at a load of 500 kg, whereas a weak weld such as that of specimen 1 illustrated in FIG. 3, shows immediate signs of elongation already at 50 kg of load. Such information can be used to screen acceptable welds without full destructive testing. For instance, if the pass parameters entered on the computer were 0.02 cm elongation at 250 kg load, then specimens #1 and #3 would be rejected and specimens 2, 4 and 5 would be acceptable.

The invention is not limited to the specifically described embodiment or examples and obvious modifications can be carried out by those skilled in the art without departing from the spirit of the invention and the scope of the following claims.

What is claimed is:

1. A method for producing an end-to-end weld and determining if the end-to-end weld has a desired level of quality, comprising the steps of: providing elongated objects having ends to be welded, wherein each elongated object is a conductor for an electrical cable; pressing said ends to be welded against one another and maintaining them in such pressed condition; welding said ends to produce the end-to-end weld; thereafter, applying a predetermined tension to the end-to-end weld; measuring elongation produced by the predetermined tension; and comparing said elongation to a preset value, thereby determining whether the end-to-end weld has the desired level of quality.

2. A method according to claim 1, wherein the comparing step is done by a computer.

3. A method for producing an end-to-end weld and determining if the end-to-end weld has a desired level of quality, comprising the steps of: providing elongated objects having ends to be welded; pressing said ends to be welded against one another in a ceramic bushing and maintaining them in such pressed condition; welding said ends under controlled time and voltage conditions to produce the end-to-end weld; thereafter, applying a predetermined tension to the end-to-end weld; measuring elongation produced by the predetermined tension; and comparing said elongation to a preset value, thereby determining whether the end-to-end weld has the desired level of quality.

4. Method according to claim 3, wherein each elongated object is a strand or a cable.

5. Method according to claim 4, further comprising the step of cooling the weld after the welding step prior to the step of applying a predetermined tension thereto.

6. A method for producing an end-to-end weld and determining if the end-to-end weld has a desired level of quality, comprising the steps of: providing elongated objects having ends to be welded; pressing said ends to be welded against one another and maintaining them in such pressed condition; welding said ends to produce the end-to-end weld; thereafter, applying a predetermined tension to the end-to-end weld; measuring elongation produced by the predetermined tension by means of strain gauges; and comparing said elongation to a preset value equal to an elongation that would be produced in a similar integral, non-welded object under the predetermined tension, thereby determining whether the end-to-end weld has the desired level of quality.

7. Apparatus for producing an end-to-end weld between elongated objects having ends to be welded and determining if the end-to-end weld has a desired level of quality, the apparatus comprises: means for pressing the ends to be welded against one another and for maintaining the ends in such pressed condition during welding; means for welding the ends to produce the end-to-end weld; means for applying a predetermined tension to the end-to-end weld; means for measuring elongation produced by said predetermined tension; and means for comprising said elongation to a preset value thereby determining whether the end-to-end weld has the desired level of quality, wherein said means for pressing the ends against each other and for maintaining the ends in pressed condition and said means for applying the predetermined tension to the weld are hydraulic cylinders.

8. Apparatus according to claim 7, further comprising means for cooling off the weld after welding and prior to applying the predetermined tension to the weld.

9. Apparatus according to claim 7, wherein the same hydraulic cylinders are used for pressing the ends against one another and for applying a predetermined tension to the weld.

10. Apparatus according to claim 7, wherein said means for measuring the elongation of the weld comprises strain gauges.

11. Apparatus according to claim 7, wherein said means for comparing said elongation to a preset value comprises a computer.

12. Apparatus according to claim 11, wherein said means for pressing the ends against each other and for maintaining the ends in pressed condition and said means for applying the predetermined tension to the weld are pneumatic cylinders.

13. Apparatus according to claim 12, wherein the same pneumatic cylinders are used for pressing the ends against one another and for applying a predetermined tension to the weld.

14. Apparatus, for producing an end-to-end weld between elongated objects having ends to be welded and determining if the end-to-end weld has a desired level of quality, the apparatus comprises: means for pressing the ends to be welded against one another and for maintaining the ends in such pressed condition during welding; means for welding the ends to produce the end-to-end weld, said means for welding said ends comprises a ceramic bushing around said ends held in place by a pair of clamps, said welding being carried out within said ceramic bushing; means for applying a predetermined tension to the end-to-end weld; means for measuring elongation produced by said predetermined tension; and means for comparing said elongation to a preset value thereby determining whether the end-to-end weld has the desired level of quality.

15. A method for determining whether an end-to-end weld in an elongated object has a desired level of quality where the end-to-end weld is produced by pressing ends of two elongated objects against one another, maintaining the ends in such pressed condition, and welding the ends to produce the end-to-end weld, the method comprising the steps of: applying a predetermined tension to the end-to-end weld; measuring elongation produced by the predetermined tension by means of strain gauges; and comparing said elongation to a preset value equal to an elongation that would be produced in a similar integral, non-welded object under the predetermined tension, thereby determining whether the end-to-end weld has the desired level of quality.

16. A method according to claim 15, wherein the comparing step is done by a computer.

17. An apparatus for determining whether an end-to-end weld in an elongated object has a desired level of quality where the end-to-end weld is produced by pressing ends of two elongated objects against one another, maintaining the ends in such pressed condition, and welding the ends to produce the end-to-end weld, the apparatus comprising: means for applying a predetermined tension to the end-to-end weld, said means for applying the predetermined tension are hydraulic cylinders; means for measuring elongation produced by the predetermined tension; and means for comparing said elongation to a preset value, thereby determining whether the end-to-end weld has the desired level of quality.

18. Apparatus according to claim 17, wherein said means for measuring said elongation comprises strain gauges.

19. Apparatus according to claim 17, wherein said means for comparing said elongation to a preset value comprises a computer.

20. Apparatus according to claim 17, wherein said means for applying the predetermined tension are pneumatic cylinders.

* * * * *

UNITED STATES PATENT AND TRADEMARK OFFICE
CERTIFICATE OF CORRECTION

PATENT NO. : 5,587,537
DATED : December 24, 1996
INVENTOR(S) : Frederick H. G. Simmons It is certified that error appears in the above-indentified patent and that said Letters Patent is hereby corrected as shown below:

Col. 4, line 43, "comprising" should be --comparing--.
Col. 5, line 5, the comma after "apparatus" should be deleted.

Signed and Sealed this

Fifteenth Day of April, 1997

Attest:

BRUCE LEHMAN

Attesting Officer      Commissioner of Patents and Trademarks